United States Patent [19]
Jones

[11] Patent Number: 5,503,616
[45] Date of Patent: *Apr. 2, 1996

[54] COLLAPSIBLE ACCESS CHANNEL SYSTEM

[75] Inventor: Jeffrey S. Jones, Salem, Va.

[73] Assignee: EndoMedical Technologies, Inc., Roanoke, Va.

[*] Notice: The term of this patent shall not extend beyond the expiration date of Pat. No. 5,386,817.

[21] Appl. No.: 177,779

[22] Filed: Jan. 5, 1994

Related U.S. Application Data

[63] Continuation-in-part of Ser. No. 42,985, Apr. 5, 1993, Pat. No. 5,386,817, which is a continuation-in-part of Ser. No. 713,178, Jun. 10, 1991, Pat. No. 5,201,908.

[51] Int. Cl.$^6$ .................................................. A61B 1/00
[52] U.S. Cl. ........................ 600/155; 600/121; 600/123; 600/127; 600/156
[58] Field of Search ................................ 128/4, 844, 917, 128/918, 919, 43; 600/121, 123, 127, 153, 156

[56] References Cited

U.S. PATENT DOCUMENTS

| | | |
|---|---|---|
| 4,406,656 | 9/1983 | Hattler et al. ................ 604/282 X |
| 4,646,722 | 3/1987 | Opie . |
| 4,721,097 | 1/1988 | D'Amelio . |
| 4,741,326 | 5/1988 | Sidall . |
| 4,779,611 | 10/1988 | Grooters . |
| 4,809,678 | 3/1989 | Klein . |
| 4,825,850 | 5/1989 | Opie . |
| 4,852,551 | 8/1989 | Opie . |
| 4,869,238 | 9/1989 | Opie . |
| 4,886,049 | 12/1989 | Darras . |
| 4,991,565 | 2/1991 | Takahashi . |
| 5,025,778 | 6/1991 | Silverstein et al. ................ 128/4 |
| 5,217,001 | 6/1993 | Nakao et al. ................ 128/4 |

FOREIGN PATENT DOCUMENTS 3508833  9/1986  Germany .

OTHER PUBLICATIONS

Beck, Marjorie L. "Is the Endoscope Hiding a 'Typhoid Mary'?"; Practical Gastroenterology, vol. XV, No. 8, p. 10.

Primary Examiner—Richard J. Apley
Assistant Examiner—Beverly M. Flanagan
Attorney, Agent, or Firm—DeWitt Ross & Stevens

[57] ABSTRACT

A channel system for use with a conventional endoscope is provided. The system comprises a collapsible access channel that is connected to a first distal end of the endoscope. The collapsible channel includes an access opening communicating between the two ends of the collapsible channel. The endoscope may be provided with a protective sheath and/or an endcap that is integral with the collapsible channel. The collapsible access channel allows a physician to insert functional instruments such as a biopsy device or tubes for supplying air, water, suction and irrigation.

10 Claims, 4 Drawing Sheets

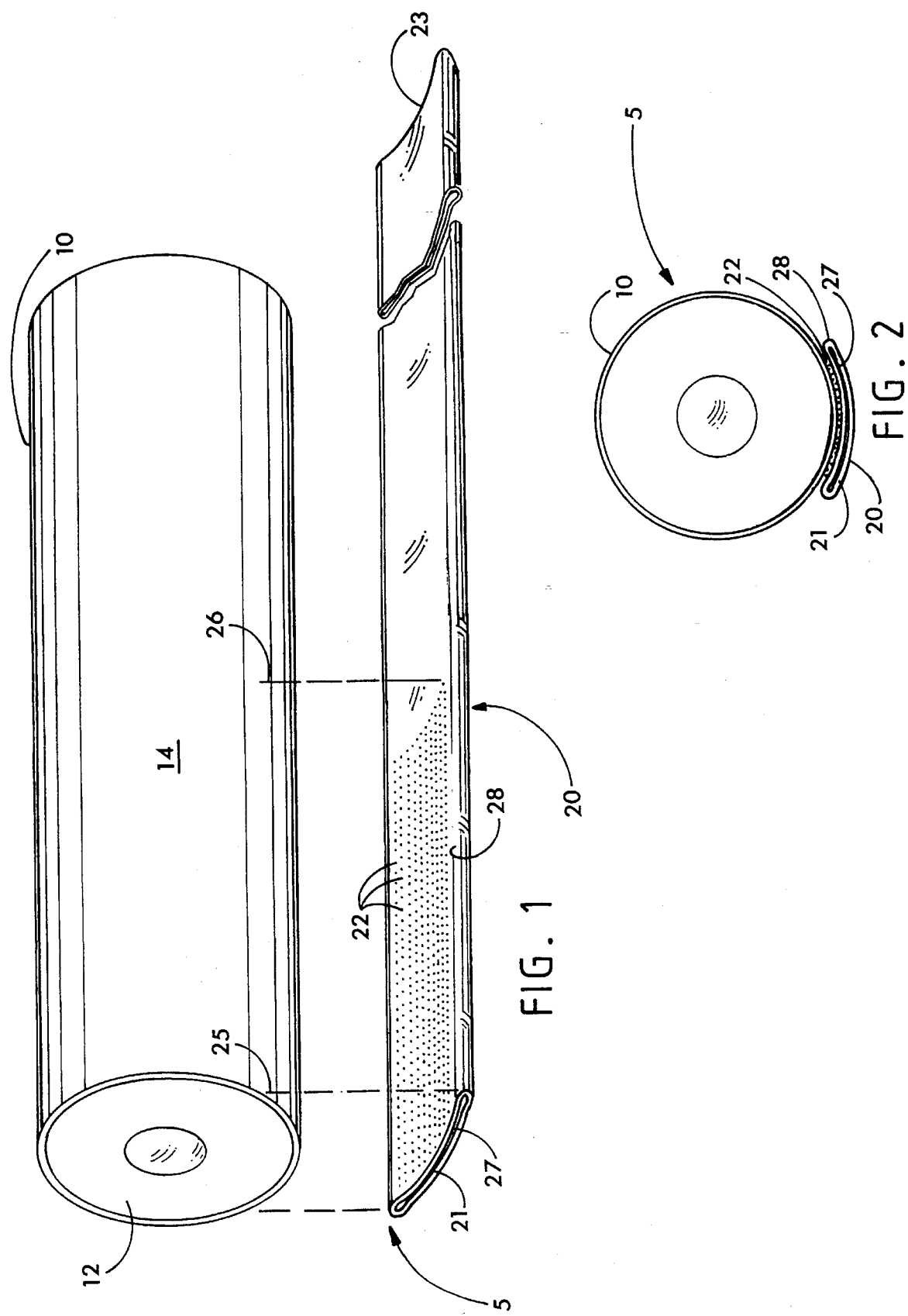

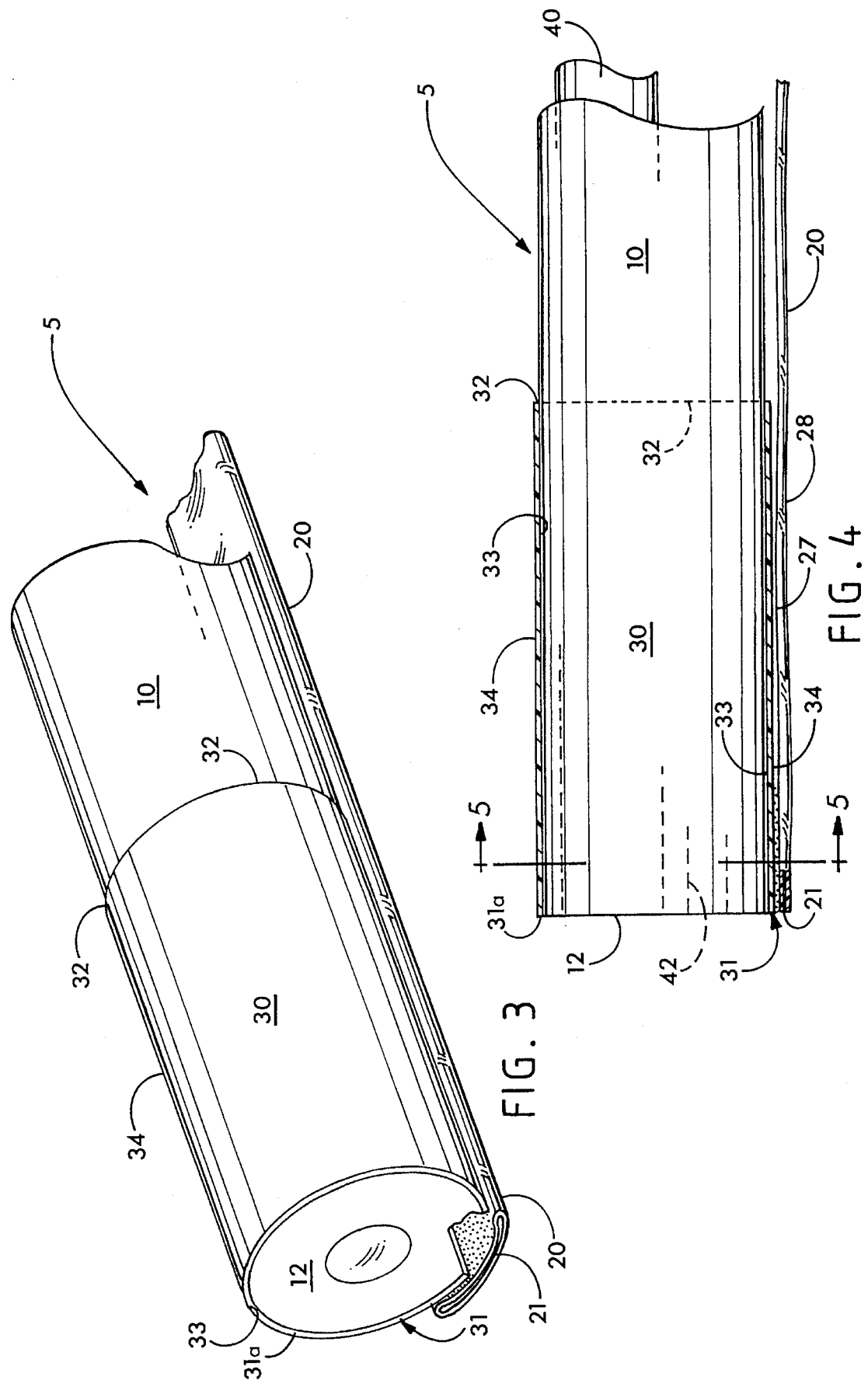

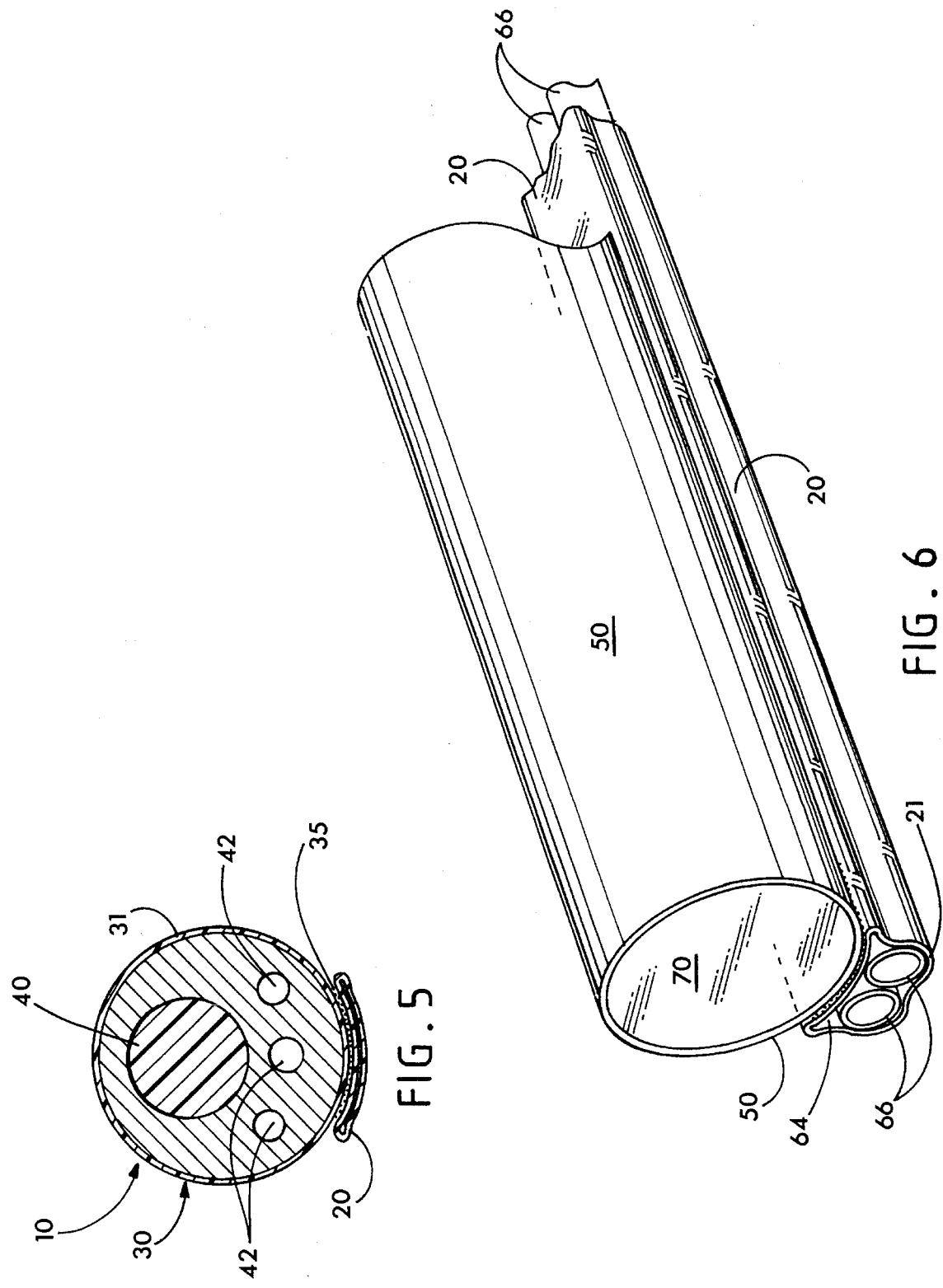

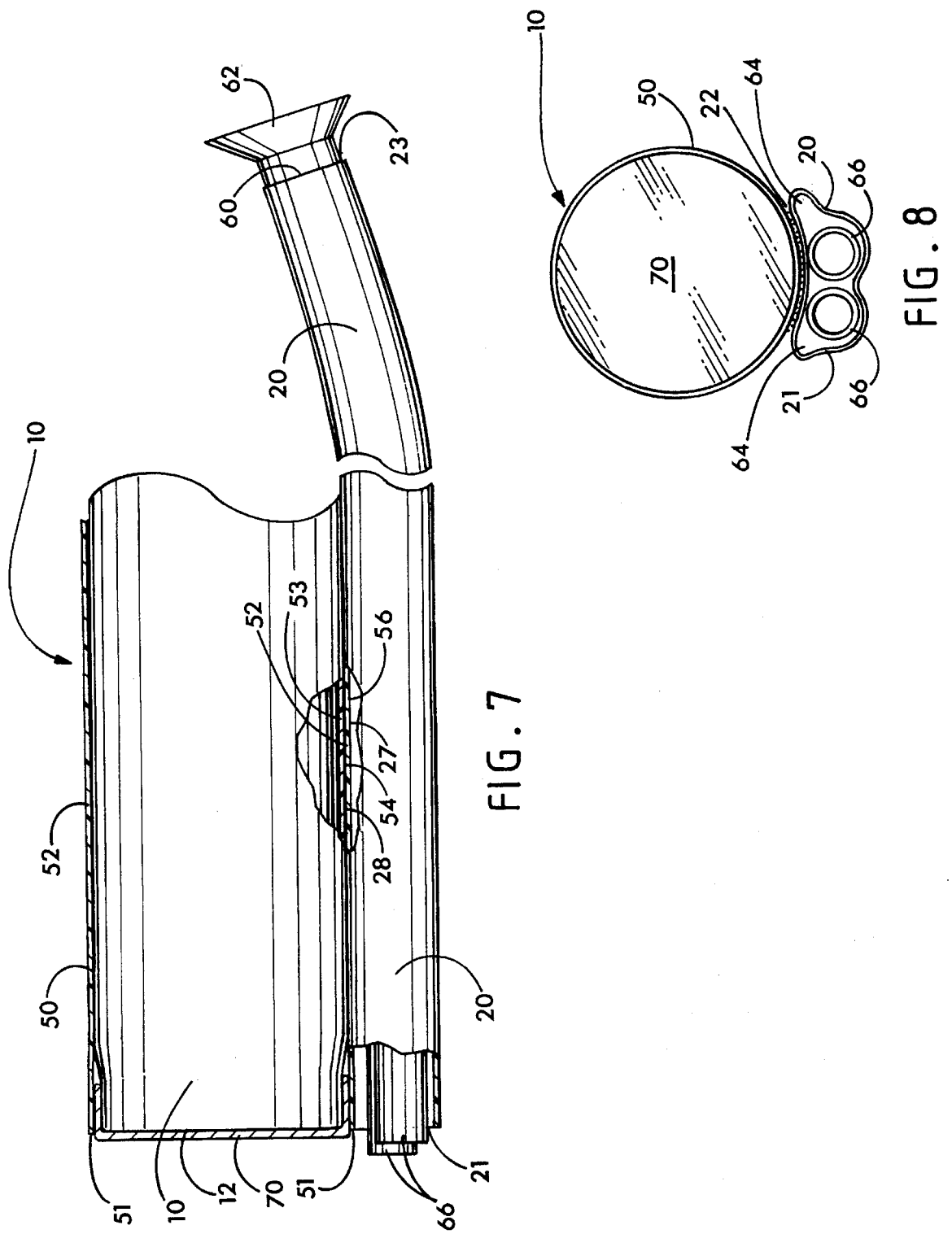

5,503,616

COLLAPSIBLE ACCESS CHANNEL SYSTEM

REFERENCE TO RELATED INVENTION

The present invention is a continuation-in-part of U.S. patent application Ser. No. 08/042,985, filed Apr. 5, 1993, now U.S. Pat. No. 5,386,817, which is a continuation-in-part of U.S. patent application Ser. No. 07/713,178, filed Jun. 10, 1991, now U.S. Pat. No. 5,201,908, both in the name of Jeffrey S. Jones, and incorporates those disclosures herein.

FIELD OF THE INVENTION

The present invention is directed to medical instruments in general and more particularly to the field of conventional endoscopes. The present invention is specifically directed to a collapsible access channel system for use with a conventional endoscope. The access channel provides a passageway for certain functions such as providing for suction, biopsy, air and water to be communicated to a patient's body cavity.

DESCRIPTION OF THE PRIOR ART

For purposes of the present invention, the term "endoscope" is intended to refer to a conventional endoscope, which includes an elongated substantially cylindrical portion, which portion is designed to enter a body cavity for examination and surgical purposes. All conventional endoscopes currently used in the market today include an elongated substantially cylindrical portion. One reason for this is to allow the distal end of the elongated portion to freely articulate in flexible endoscopes. Any shape other than a substantially cylindrical shape would hinder the required flexibility of the distal end. There are also rigid endoscopes which are substantially cylindrical but do not have an articulating distal end.

Endoscopes allow a physician to observe a body cavity and to insert medical instruments into the cavity for a variety of purposes. Medical instruments may take the form of many types of devices, for example, a biopsy device, an air tube, an irrigation tube and a suction tube.

Conventional endoscopes may also be fitted with a protective covering. Sanitary disposable protective coverings are used with endoscopes to shield the endoscope from a patient's body which may carry bacteria or viruses. These devices are known to the prior art. For example, reference is made to U.S. Pat. No. 5,201,908 to Jones which is incorporated herein by reference and is directed to a protective covering for a medical instrument, such as an endoscope. The covering includes an elongated hollow sheath having a wall of flexible material. The sheath includes auxiliary access tubes, providing a variety of functions, such as instrument manipulation and fluid removal.

In all endoscopy the main feature is to gain access to the body cavity being examined using the smallest diameter endoscope possible. With the present state of the art, this means that the size of the access channels and the subsequent instruments introduced is severly limited. All present scopes have the access channels built within the cylindrical confines of the scope. This limits the size of the instrument that can be introduced into the body cavity at any one time.

SUMMARY OF THE INVENTION

The present invention is designed to overcome the deficiencies of the prior art by providing a channel system for use with both flexible and rigid conventional endoscopes. The present invention will allow a smaller scope to gain access to a body cavity. Once access has been gained it is usually a simple procedure to dilate the cavity or orifice to allow entry of larger instruments or devices. The endoscope includes an elongated, substantially cylindrical portion having a first distal end and a second proximal end. The channel system comprises a collapsible channel with a first distal end and a second proximal end and is adapted to extend alongside and exterior to the cylindrical portion of the endoscope. The collapsible channel is provided with an access means communicating between the first end and the second end of the collapsible channel. The system also includes a means to attach the collapsible channel to the endoscope.

The invention is further directed to a channel system in combination with a conventional endoscope having an elongated, substantially cylindrical portion with a first distal end and a second proximal end. The channel system includes an endcap designed to fit over the first distal end of the of the endoscope. A collapsible channel is provided which is integral with the endcap. The collapsible channel is adapted to extend alongside and exterior to the elongated, substantially cylindrical portion of the endoscope. The system further provides for a passageway between the first and second ends of the collapsible channel.

An advantage of the collapsible access channel system is that it provides an auxilliary channel attachment for a standard endoscope. Thus, prior art endoscopes can be provided with a channel system allowing a passageway for instruments into a body cavity.

Further, the collapsible access channel of the present invention provides a means to allow more and/or larger instruments to be placed in a body cavity. An endoscope with the attached access channel in collapsed form is first inserted into the body orifice. After insertion an instrument, generally in the form of a tube or a biopsy mechanism, may be inserted into the access channel. As the instrument is moved along the access channel, the elasticity of the channel enables the channel to enlarge and conform to and fit the instrument. The body orifice also naturally dilates to conform to the enlarged access channel. The collapsible channel, therefore, provides a variable sized entrance into the body orifice depending upon the medical procedures that are required.

Additionally, more than one access channel may be attached to the endoscope. With several access channels, a variety of functional tubes and medical instruments may be inserted into the body cavity at one time to perform different functions. The body orifice or cavity will be dilated by the passage of additional devices through accessory channels. When the additional devices are inserted, the endoscope with an access channel attached will have a larger cross section than a naked endoscope. In the prior art, the access channels are rigid, necessitating a large initial endoscope cross-section which may hamper the insertion of the endoscope into the desired location.

Further objects, features and advantages of the invention will be apparent from the following detailed description when taken in conjunction with the accompanying drawings.

BRIEF DESCRIPTION OF THE DRAWINGS

FIG. 1 is a perspective view illustrating the collapsed channel with adhesive before attachment to an endoscope.

FIG. 2 is an elevated end view of the collapsed channel of FIG. 1 adhesively attached to an endoscope.

FIG. 3 is a perspective partial cutaway view of an alternative embodiment of the present invention showing an endcap with a collapsed access channel attached thereto placed on the distal end of an endoscope.

FIG. 4 is a side elevated view of embodiment illustrated in FIG. 3.

FIG. 5 is a cross-sectional elevated view along lines 5—5 of the collapsed channel shown in FIG. 4.

FIG. 6 is a perspective view of another embodiment of the present invention illustrated a now-expanded access channel integral with a protective sheath covering an endoscope.

FIG. 7 is a side elevated partial cutaway view of the embodiment illustrated in FIG. 6.

FIG. 8 is an end elevated view of the embodiment of FIG. 6.

DETAILED DESCRIPTION OF THE INVENTION

The present invention is generally directed for use with any medical instrument having an elongated tubular portion. The present invention is particularly applicable to a conventional endoscope having a substantially cylindrical or tubular portion. Depending upon the use of the endoscope, the endoscope tubular portion can vary in length from approximately 1–6 feet and is designed to enter a body cavity for examination and surgical purposes.

Specifically, the present invention is directed to an auxilliary channel system which may be applied to a variety of conventional endoscopes for examining the body. A collapsible access channel can be used with any flexible gastrointestinal scope or rigid instrument. Such examples include cytoscopes, upper endoscopes for the examination of the esophagus, stomach and duodenum, colonoscopes for examining the colon, angioscopes for examining blood vessels, bronchoscopes for examining the bronchi, laparoscopes for examining the peritoneal cavity, and arthroscopes for examining joint spaces.

Reference is now made to the figures where the same reference numerals refer to like features. FIG. 1 illustrates a channel system 5 with a collapsible channel 20 designed for attachment to a conventional, flexible basic endoscope 10 commonly used in the medical field. The construction of the endoscope 10 is well-known to the art and does not form a part of this invention. Reference is made to U.S. Pat. No. 4,809,678 to Klein, U.S. Pat. No. 4,825,850 to Opie et al., and U.S. Pat. No. 4,852,551 also to Opie et al. for a variety of descriptions for endoscopes. The endoscope 10 includes a first distal end 12 and a substantially cylindrical elongated flexible portion 14. The remainder of the endoscope is not illustrated.

In one of the preferred embodiments, the access channel 20, as shown in FIG. 1, is collapsed upon itself. The collapsible channel 20 has a first distal end 21, a second end 23, an inner wall surface 27, an outer wall surface 28. The access channel is made from a flexible, or more specifically ductile, material which may be elastomeric in the preferred embodiment. The component materials may be made from elastomeric material including polymeric resinous materials such as natural and synthetic rubbers, thermoplastic polymeric materials such as polyethylene, polypropylene, polyurethane, and combinations of natural or synthetic rubbers with thermoplastic polymeric materials such as rubber, modified polyethylene, rubber-modified polystyrene and the like. The length of the collapsible channel 20 is adjustable, but preferably similar in length to the length of the endoscope 10.

The access channel 20 is preferably adhered to the endoscope 10 by an adhesive material 22 as shown in FIGS. 1 and 2. Adhesive materials are known to the art and, by themselves, do not form a part of the invention. The adhesive material 22 is designed to be applied to the outer surface 28 of the collapsible channel 20. In alternate embodiments, the adhesive material 22 may be applied to the collapsible channel 20 as well as to the endoscope 10 or to the endoscope 10 only, where the collapsible channel 20 is to be attached. In the preferred embodiment, the adhesive material 22 applied to the outer surface 28 is attached to the endoscope 10 near the first distal end 12 between points 25 and 26. The collapsible channel 20 may also be attached to the endoscope 10 near the first distal end 12 between other points by any conventional means known to the art such as velcro, welding, or an attachment band.

In a preferred embodiment, the adhesive material 22 is a temporary connection to the endoscope 10 and the attachment may be released by pulling the collapsible channel 20 away from the endoscope 10 after it has been used. The adhesive material 22 positions the first end 21 of the collapsible access channel 20 near the first end 12 of the endoscope 10 such that the remaining unattached portion of the collapsible channel 20 is freely dissociated from the remaining portion of the endoscope 10. However, when the endoscope 10 is inserted into a body cavity, the collapsible access channel first end 21 which is attached to the endoscope first end 12 is inserted concurrently, trailing the remaining portion of the collapsible channel 20 which enters the body orifice adjacent and along with the endoscope 10. The collapsible channel 20 may be positioned within the orifice protruding into the body cavity a distance as far as required by the surgeon and as far as the endoscope 10 to perform the medical function required.

A significant feature of the collapsible channel 20, as shown in FIGS. 1 and 2, is its ability to collapse upon itself and then be inserted into a body orifice entering a body cavity in a flattened form. Once positioned inside the body cavity, an instrument or instruments may be inserted into the flattened collapsible channel 20. Upon insertion of such instrument at the second end 23, the collapsible channel 20 will expand around the instrument, to size, fitting tightly adjacent and conforming to the instrument through the body orifice. The expanded collapsible channel 20 adapts the body orifice, enlarging it and conforming it around the expanded collapsible channel 20. An advantage of this procedure is that the collapsible channel 20 allows large instruments to be placed within the collapsible channel 20 adjacent the inner wall 27 which provides a passageway 64, shown in FIG. 8, at the second end 23 communicating to a body cavity at the first end 21, when inserted. This is possible because a body orifice will enlarge slowly, not abruptly. Since the channel system 5 allows instruments to be inserted one at a time, a slow orifice dilation can occur, without tissue tearing.

In an alternate embodiment, an endoscope endcap 30 may also be provided, as illustrated in FIGS. 3–5, to fit over the first distal end 12 of the endoscope 10 and provide a means to releasibly attach the access channel 20 to the endoscope 10. In this embodiment, the endcap 30 only covers the distal end 12 of the endoscope 10. The endcap 30 has a first distal end 31, a second proximal end 32, an inner wall 33 and an outer wall 34. The distal end 31 of the endcap 30 may be provided with a window (not shown) covering the distal end 12 of the endoscope or a fitting ridge 31a which prevents the endcap 30 from sliding along the length of the endoscope 10.

The endcap 30 can be made of a number of materials known to the art. For example, the endcap may be formed from elastomeric materials which are flexible, such as, polyethylene, polypropylene, polyurethane and combinations of natural or synthetic rubbers with thermoplastic polymeric materials similar to materials used for the collapsible channel 20. The endcap 30 may also be constructed of semi-rigid or rigid plastic or rubber material, to form some structural integrity over the end of the endoscope 10. Preferred examples of materials include styrene, plexiglass and polyvinyl chloride.

As illustrated in FIG. 5, the endcap 30 surrounds the distal end 12 of the endoscope 10. The endoscope is illustrated with conventional parts including a main endoscope viewing channel 40 and at least one and preferably three access tubes 42 which are part of the endoscope.

In operation, the access channel 20 adhesively adheres to the endcap 30 as described above with respect to FIGS. 1–2. The endcap 30 is slidably placed over the distal end 12 of the endoscope 10. The endoscope 10 with the attached access channel 20 is now ready for use.

In another embodiment, shown in FIGS. 6–8, substantially all of the endoscope 10 is covered with a covering or sheath 50 as described in U.S. Pat. No. 5,201,908 to Jones, which is incorporated herein by reference. The sheath 50, is a flexible, loose-fitting covering designed to be placed over the endoscope 10. Substantially impervious to gas and water, the sheath 50 protects the endoscope 10 from the invasion of contaminants. The sheath 50 material can be elastomeric made from similar materials as described earlier for the collapsible channel 20.

The sheath 50 has a wall 52 including an inner wall surface 54 and an outer wall surface 56 and is integral with the collapsible access channel 20. The collapsible access channel 20 extends in axial fashion along the wall 52 of the sheath 50 from the first end 51 to a second end 60, shown in FIG. 7. The sheath 50 is also provided with an endcap 70 over the first end 12 of the endoscope 10. The endcap 70 provides structural integrity and protection for the end of the endoscope 10.

The access channel 20, shown in FIG. 7, is integral with the sheath 50 along the entire length of the sheath 50 but extends further than the sheath 50 from the first end 21 to the second end 23. The word integral, in this context, means that the outer wall 28 of the access channel 20 is identical to the sheath inner wall surface 54 and that the channel inner wall surface 27 is identical to the sheath outer wall surface 56, as shown in FIG. 7 within the broken section. The broken section also shows that the sheath wall 52 is located adjacent an endoscope wall 53. The second end 23 provides an opening 60 sized to receive a device such as a funnel 62 to provide an access means, or passageway 64, as shown in FIGS. 6 and 8, for a variety of tubes 66 such as suction tubes, water tubes or air tubes, or instruments to be inserted into the opening 60 and the access channel 20. Since the collapsible channel 20 may be dimensioned with a passageway 64 diameter larger than the endoscope 10 diameter, there are many devices available to a physician that could be placed within the collapsible channel 20 for access into a body cavity.

The channel system 5 may comprise, in alternate embodiments, a plurality of collapsible access channels 20. The plurality of access channels 20 may be separate tubular collapsible channels extending axially along the endoscope 10 to allow more than one instrument or fluid tube to be used concurrently. The access channel 20 may extend alongside the endoscope 10 preventing contamination of the air, water, suction, and biopsy tubes, avoiding the necessity of cleaning and sterilizing the instruments.

A method of using the collapsible channel 20 will now be described. In the illustrated embodiments, a collapsible access channel 20 is depicted with an endoscope 10. Many of the newer endoscopes are small, for instance, 4–5 mm. in circumference. These tiny scopes will allow a collapsed, flexible access channel 20 with a diameter that is larger than the endoscope 10 diameter to be attached to the scope and inserted into a body cavity with the endoscope 10. The access channel 20, in its collapsed, compact form, (shown in FIGS. 1–5), is inserted into a body cavity attached to an endoscope 10. Instruments, such as biopsy tools, fluid tubes and suction tubes, etc. are then inserted into the funnel 62 and eased along the passageway 64 one at a time toward the first end 21. As the instrument, or tube 66, passes the cavity orifice, the collapsible channel 20 conformably expands, as shown in FIGS. 6–8, to receive the instrument. The orifice dilates to allow the collapsible channel 20 to expand around the inserted tube 66. The collapsible channel 20 and the body orifice both conform to the increased circumference without tearing. In this manner, the inserted instrument or tube 66 may be manipulated by a surgeon to perform a medical task, such as a biopsy, or regulating fluid flow.

It is understood that the invention is not confined to the particular construction and arrangement herein illustrated and described, but embraces such modified forms thereof as come within the scope of the following claims.

What is claimed is:

1. An access channel system in combination with a conventional endoscope, wherein the endoscope includes an elongated, substantially cylindrical portion having a first distal end and a second proximal end, the access channel system comprising:

a. a collapsible access channel having a first end and a second end, the access channel being adapted to extend freely alongside and exterior to the substantially cylindrical portion;

b. access means within the access channel communicating between the first end and the second end of the access channel; and c. means to attach the first end of the access channel to the first distal end of the endoscope;

wherein the access channel, once attached to the first distal end of the endoscope, is unattached to the remaining portion of the substantially cylindrical portion of the endoscope so that it may freely move over the surface thereof.

2. The system of claim 1 wherein the endoscope is provided with a protective sheath adapted to encompass the elongated portion of the endoscope, the sheath including an endcap adapted to releasably fit over the first end of the endoscope.

3. The system of claim 2 wherein the access channel is connected to the protective sheath.

4. The system of claim 3 wherein the access channel is connected to the endcap of the protective sheath.

5. The system of claim 1 wherein the access channel includes a plurality of channels.

6. An access channel system in combination with a conventional endoscope, wherein the endoscope includes an elongated, substantially cylindrical portion having a first end and a second end, the channel system comprising:

a. a protective sheath adapted to encompass the elongated portion of the endoscope, the sheath including an endcap adapted to releasably fit over the first end of the endoscope;

b. a collapsible access channel having a first end and a second end, the access channel being attached to the endcap and opening thereupon, the access channel being adapted to extend freely alongside and exterior to the elongated, substantially cylindrical portion of the endoscope when the endcap is releasably fit over the first end of the endoscope; and c. a passageway between the first end and the second end of the access channel providing access to a body cavity;

wherein the access channel is disassociated from the sheath apart from the endcap, and further wherein the access channel is unattached to the substantially cylindrical portion of the endoscope, thereby the access channel is allowed to freely move beneath the sheath and over the surface of the substantially cylindrical portion of the endoscope after the endcap is releasably fit over the first distal end of the endoscope.

7. The system of claim 6 wherein the access channel includes a plurality of channels.

8. An access channel system for use with a conventional endoscope, wherein the endoscope includes an elongated, substantially cylindrical portion having a first end and a second end, the channel system comprising:

a. an endcap adapted to releasably fit over the first end of the endoscope; and b. a collapsible access channel attached to and opening upon the endcap, the access channel having a first end and a second end, the access channel being adapted to extend freely alongside and exterior to the elongated, substantially cylindrical portion of the endoscope when the endcap is releasably fit over the first end of the endoscope;

wherein the access channel is unattached to the substantially cylindrical portion of the endoscope so that it may freely move over the surface of the substantially cylindrical portion of the endoscope after the endcap is releasably fit over the first distal end of the endoscope.

9. The access channel system of claim 8, wherein the endcap is formed from substantially rigid material.

10. The access channel system of claim 8, wherein the endcap is formed from substantially flexible elastomeric material.

* * * * *